United States Patent [19]

Hann et al.

[11] Patent Number: 4,492,578
[45] Date of Patent: Jan. 8, 1985

[54] PLASTIC LAMINAR DIGITALLY INDEXED DENTAL DIE SYSTEM

[76] Inventors: William Hann, 325 Ashlawn Dr.; Sanford D. Bosin, P.O. Box 9371, both of Norfolk, Va. 23505; Cecil White, 1464 Longdale Dr., Norfolk, Va. 23513

[21] Appl. No.: 511,748

[22] Filed: Sep. 29, 1983

[51] Int. Cl.³ .................... A61C 11/00; A61C 13/02; B32B 3/00

[52] U.S. Cl. .................... 433/213; 249/54; 249/112; 249/115; 428/156

[58] Field of Search .................... 264/16–18, 264/313; 249/54, 112, 115; 428/138, 133, 156; 52/127.3, 127.5, 250, 268, 269, 177, 129, 452, 454, 506, 511, 378, 410, 443, 444, 598, 612, 733; 433/213

[56] References Cited

U.S. PATENT DOCUMENTS

| | | | |
|---|---|---|---|
| 1,079,540 | 11/1913 | Clapp et al. | 433/56 |
| 2,037,545 | 4/1936 | Sexton | 52/598 |
| 2,573,482 | 10/1951 | Pelk | 52/443 |
| 3,575,764 | 4/1971 | McFarren | 428/156 |
| 3,838,187 | 9/1974 | Thomas | 264/17 |
| 3,937,773 | 2/1976 | Huffman | 264/17 |
| 4,050,756 | 9/1977 | Moore | 428/133 |
| 4,238,189 | 12/1980 | Tirino | 266/16 |
| 4,368,042 | 1/1983 | Felstead et al. | 433/213 |

FOREIGN PATENT DOCUMENTS 0044223  1/1982  European Pat. Off. ............ 433/49

Primary Examiner—Willard E. Hoag

[57] ABSTRACT

A device for construction of removable dental dies fabricated from type IV dental die stone poured into non-rigid impression materials. The device eliminates the need for a two pour system necessitated when individual pins are used, provides large surface area for positive seating of the individual dies, and in general eliminates the complicated alignment problems associated with other systems in common use. The invention comprises a polymer sheet having projections on both sides for embedment in dental store of the date of the die and base.

3 Claims, 8 Drawing Figures

PLASTIC LAMINAR DIGITALLY INDEXED DENTAL DIE SYSTEM

The present invention provides a means of both indexing and separating removable dental stone dies from the adjacent portions of a quadrant or full arch dental stone model.

The device consists of a twin sheet of polymer plastic having round conical projections on one side and round inverted conical projections on the opposite side. The projections are uniform in size and shape and spaced at regular intervals.

Figure 1:
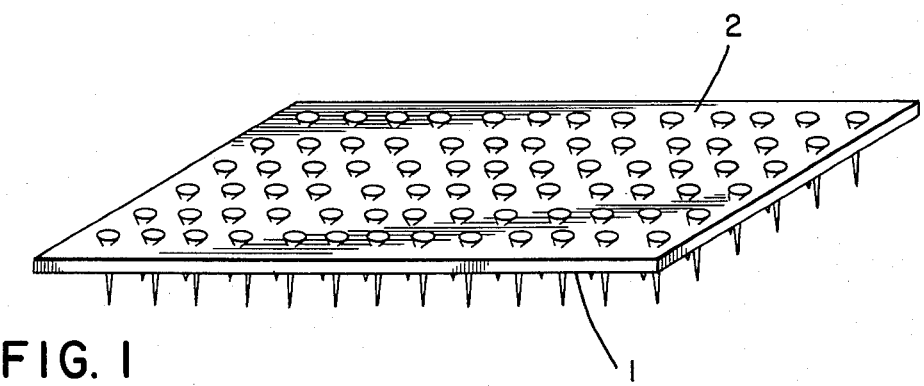
FIG. 1 is a ¾ view of the plastic sheet having inverted or undercut projections on the retentive side 2 and conical projections on the indexing side 1. The inverted conical projections provide undercuts for retention of the plastic sheet when submerged in the dental die stone.
Figure 2:
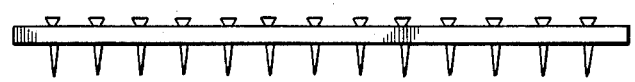
FIG. 2 is a side view of the plastic sheet indicating undercut projections on side 2 and conical projections on the reverse, side 1.
Figure 3:
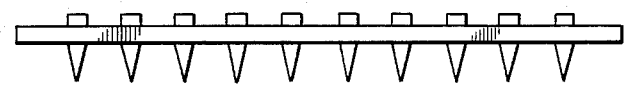
Figure 4:
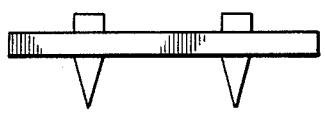
Figure 5:
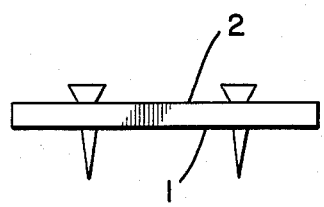

The device may be manufactured in the configuration indicated in FIG. 2 using conventional molding techniques if a flexible mold is used. This is necessitated to facilitate removal of the undercut projections from the mold. If on the other hand a rigid mold is used, the plastic sheet would be produced as indicated in FIG. 3 and in the enlarged view FIG. 4. The undercuts on the retentive side are then either machined into the projections or the projections are heated and depressed to produce the configuration indicated in the side view of FIGS. 5-2.

Figure 6:
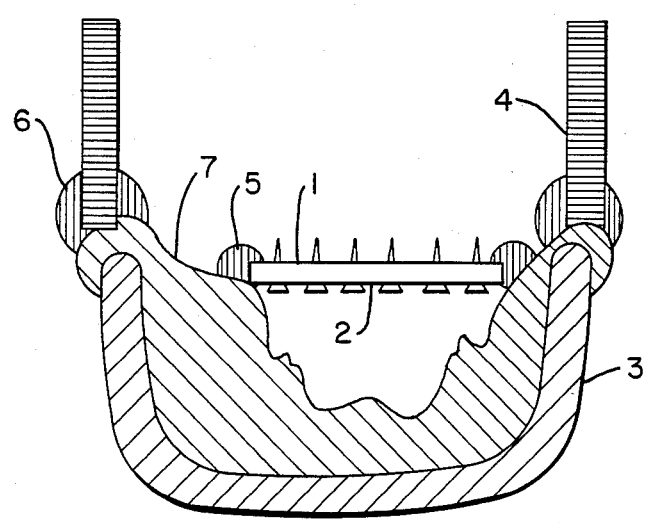

FIG. 6 is a cross sectional view illustrating the use of the die system with a conventional impression and model pouring technique. The impression tray 3, containing a non-rigid impression 7 is prepared for pouring with stone die material. The illustration in FIG. 6 indicates the commonly employed "beading and boxing" of the impression with beading wax 6 and boxing wax 4. A section of the is cut which will fit the width and length of the portion of the impression from which the dies are to be fabricated. The prepared section of the indexing sheet is then affixed to the impression material in such a manner as to be perpendicular to the desired path of withdrawal of the removable die. Wax or any suitable luting agent 5 is used to secure the indexing sheet to the impression material. The sheet is oriented so that the retentive side 2 faces the impression material 7 and the indexing side 1 will face the base of the completed model FIGS. 7-11.

Figure 7:
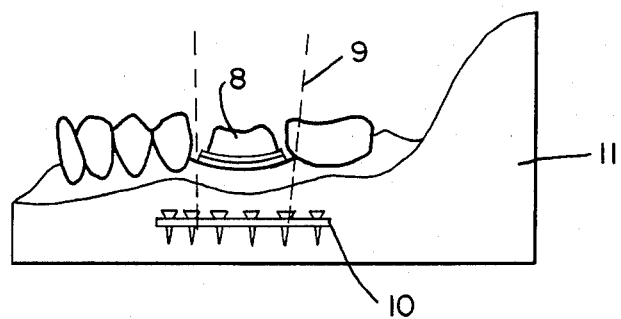

FIG. 7 indicates the poured die model after separation from the impression and illustrates the submerged indexing sheet 10. The broken lines 9 indicate the path of the saw cuts which will be made to separate the prepared tooth 8 from the completed die model.

Figure 8:
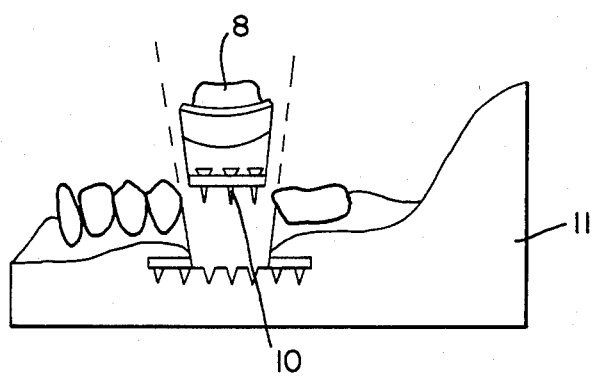

FIG. 8 indicates the removal of the die 8 with the index 10 attached to its base after saw cuts have been completed. The conical projections on the index 10 provide for accurate replacement of the die 8 into the model 11.

The system eliminates many pitfalls inherent in the other commonly used methods of die construction.

I. The most common method involves the use of dowel pins, which consists of a tapered conical brass pin having one side flattened. The retentive end of the pin is knurled so as to be mechanically retained in the dental die stone. This pin must be alaigned and held into place over the impression of the prepared tooth during the initial pour. Sufficient die stone is poured into the impression so as to engulf only the knurled end of the pin. A separating medium must then be placed on the exposed portion of the stone which overlies the prepared tooth, and a second pour is made to engulf the conical portion of the pin. Provisions must be made to insure that the second pour of stone is retained to the first except in the vivinity of the portion that represents the prepared tooth. Saw cuts are then made to release the die. This method requires two pours of stone, necessitates time consuming alignment of the pins, and the finished die is prone to inaccuracy because of the limited surface area on the flattened portion of the pin which is intended to prevent rotation of the die.

II. The so-called die-lock tray requires that the die model be poured and trimmed to fit the tray. A second pour is then required to adapt the die model to the tray. The tray is then separated, the die portion of the model is sawed, and the pieces are re-oriented and replaced in the tray. Problems associated with this method involve the need for tedious trimming of the die model for adaptation to the tray as well as inaccuracies associated with reassembly of the constituent parts after they have been sawed apart.

III. The pindex and pin mate systems both involve the use of a pin arrangement which is retained in the die portion of the model as a precision sleeve into which the pin fits. The sleeve is retained by a second pour of stone, and in both cases, complicated measures are necessary for alignment of the pins and a second pour is necessary to retain the sleeve' portion of the system. The surface area which provides a positive seat for vertical orientation of the die is limited, which reduces the accuracy of the system. In addition, a separating medium must be employed to insure separation of the die model.

IV. The "Logix" system involves the use of a plastic tubular insert which is affixed to the impression. The tube becomes submerged in the die stone, and serves as both the separating medium and the indexing device. The problems associated with this system include the fact that the plastic tube is difficult to locate within the substance of the stone model in order to make saw cuts for separation. The method produces a die which is very fragile, difficult to separate, and has an extremely limited surface area to provide a positive vertical seat.

V. The present system, avoids the necessity for two pours. The laminar nature allows it to function as both the separating medium and the indexing system. The flat sheet interspersed between the conical projections provides a large surface area to insure a positive vertical stop which insures accurate removal and replacement of the die portion of the model. The fact that the system utilizes numerous conical projections rather than a single pin precludes rotational inaccuracies in the fabrication of the die. Because the sheet can be cut to the desired size and easily oriented and affixed to the impression, it eliminates many of the time consuming aspects of die fabrication. The location of the indexing system within the substance of the stone is easily determind because the laminar sheet extends to the facial and lingual aspects of the impression. The numerous undercut projections on the retentive side preclude failure of the mechanical bond between the stone and the retentive end of conventional pin systems. The need to use adhesives for retention of the pins is also eliminated.

What I claim is:

1. A device for keying a dental model to a dental model base comprising:

a polymeric sheet having a generally flat web portion and having projections extending from opposite sides of said web portion, said projections from a first of said sides being in the shape of cones with broad base portions of said cones being connected to said web portion and tips of said cones being spaced from said web portion and said projections from a second of a said sides having broad end portions spaced from said second of said sides.

2. A dental model base having at least partially embedded therein a polymeric strip having a generally flat web portion and projections extending from a first of opposite sides being conical and having broad base portions connected with said web portion and tips of said projections being spaced from said first of said sides; projections from a second of said sides having broad end portions spaced from said second of said sides.

3. The article of claims 1 or 2 wherein said projections from said second side of said web portion have undercut sides.

* * * * *

UNITED STATES PATENT AND TRADEMARK OFFICE
CERTIFICATE OF CORRECTION

PATENT NO. : 4,492,578
DATED : January 8, 1985
INVENTOR(S) : William Hann et al.

It is certified that error appears in the above-identified patent and that said Letters Patent is hereby corrected as shown below:

On the title page,

ABSTRACT, line 10, "sides for embedment in dental store of the date of the die" should read -- sides for embedment in dental stone of the die --.

Signed and Sealed this

Eighteenth Day of June 1985

[SEAL]

Attest:

DONALD J. QUIGG

Attesting Officer

Acting Commissioner of Patents and Trademarks